US007799344B2

United States Patent
Oberg (10) Patent No.: US 7,799,344 B2
(45) Date of Patent: *Sep. 21, 2010

(54) METHOD OF DRUG FORMULATION BASED ON INCREASING THE AFFINITY OF CRYSTALLINE MICROPARTICLE SURFACES FOR ACTIVE AGENTS

(75) Inventor: Keith A. Oberg, Valencia, CA (US)

(73) Assignee: MannKind Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/532,063

(22) Filed: Sep. 14, 2006

(65) Prior Publication Data

US 2007/0059373 A1 Mar. 15, 2007

Related U.S. Application Data

(60) Provisional application No. 60/717,524, filed on Sep. 14, 2005, provisional application No. 60/744,882, filed on Apr. 14, 2006.

(51) Int. Cl.
*A61K 9/14* (2006.01)
*A61K 9/28* (2006.01)
*A61K 38/28* (2006.01)

(52) U.S. Cl. ....................... 424/489; 424/490; 424/491; 424/499; 424/434; 514/2; 514/3

(58) Field of Classification Search ....................... None
See application file for complete search history.

(56) References Cited

U.S. PATENT DOCUMENTS

| | | | | |
|---|---|---|---|---|
| 5,105,291 | A * | 4/1992 | Matsumoto et al. | 349/139 |
| 5,352,461 | A | 10/1994 | Feldstein et al. | |
| 5,503,852 | A | 4/1996 | Steiner et al. | |
| 5,679,377 | A * | 10/1997 | Bernstein et al. | 424/491 |
| 6,043,214 | A | 3/2000 | Jensen et al. | |
| 6,071,497 | A | 6/2000 | Steiner et al. | |
| 6,440,463 | B1 | 8/2002 | Feldstein et al. | |
| 6,444,226 | B1 * | 9/2002 | Steiner et al. | 424/489 |
| 6,652,885 | B2 | 11/2003 | Steiner et al. | |
| 6,884,435 | B1 | 4/2005 | O'Hagan et al. | |
| 7,048,908 | B2 | 5/2006 | Basu et al. | |
| 2003/0013641 | A1 | 1/2003 | Steiner et al. | |
| 2004/0234615 | A1 * | 11/2004 | Sabetsky | 424/493 |
| 2004/0234616 | A1 * | 11/2004 | Sabetsky | 424/493 |
| 2005/0153874 | A1 | 7/2005 | Cheatham et al. | |
| 2006/0260777 | A1 * | 11/2006 | Rashba-Step et al. | 162/181.1 |
| 2007/0059374 | A1 | 3/2007 | Hokenson et al. | |

FOREIGN PATENT DOCUMENTS

| | | | |
|---|---|---|---|
| EP | 1 060 741 | A1 | 12/2000 |
| WO | 96/13250 | | 5/1996 |
| WO | 96/13250 | A1 | 5/1996 |
| WO | 02/058735 | A1 | 8/2002 |
| WO | 02/067995 | | 9/2002 |
| WO | 02/067995 | A1 | 9/2002 |
| WO | 2005/020964 | A1 | 3/2005 |

* cited by examiner

*Primary Examiner*—Julie Ha
(74) *Attorney, Agent, or Firm*—K&L Gates LLP; Louis C. Cullman; Michelle Glasky Bergman

(57) ABSTRACT

Methods are provided for coating crystalline microparticles with an active agent by altering the surface properties of the microparticles in order to facilitate favorable association on the microparticle by the active agent. Type of surface properties that are altered by the disclosed methods include by electrostatic properties, hydrophobic properties and hydrogen bonding properties.

18 Claims, 7 Drawing Sheets

METHOD OF DRUG FORMULATION BASED ON INCREASING THE AFFINITY OF CRYSTALLINE MICROPARTICLE SURFACES FOR ACTIVE AGENTS

CROSS REFERENCE TO RELATED APPLICATIONS

The present application claims the benefit under 35 U.S.C. §119(e) to U.S. Provisional Application Ser. No. 60/717,524 filed on Sep. 14, 2005, and U.S. Provisional Application Ser. No. 60/744,882, filed on Apr. 14, 2006, the entire contents of which are hereby incorporated by reference in their entirety.

FIELD OF THE INVENTION

This invention is generally in the area of drug formulations and is particularly related to methods of coating active agents onto the surface of crystalline microparticles.

BACKGROUND OF THE INVENTION

Delivery of therapeutic agents has been a major problem. Oral administration is one of the most common and preferred routes of delivery due to ease of administration, patient compliance, and decreased cost. However, the disadvantages of this route include low or variable potency and inefficient adsorption of the therapeutic. This is particularly evident when the compound to be delivered is unstable under conditions encountered in the gastrointestinal tract. A variety of coatings and encapsulation methods have been developed in the art, but only a few are effective in addressing this issue. Still, there are therapeutic compounds that tend to be less active in the conditions of the gastrointestinal tract and must be administered in higher dosages to be adsorbed into the bloodstream in an effective amount.

A broad range of drug formulation systems have been developed to address the problem of optimal drug delivery and are based on incorporation of drug into a matrix that acts as a carrier. Factors considered in drug formulation include requirements that the system be non-toxic, non-reactive with the drug to be delivered, economical to manufacture, formed of readily available components, and consistent with respect to final composition and physical characteristics, including stability and release rate. It is also preferable that the drug delivery system is formed of materials easily removed from the body by normal physiologic processes.

Microparticle drug formulations can be used in numerous routes of administration, but are particularly well suited to pulmonary delivery. Advantages of the lungs for delivery of agents having systemic effects include the large amount of surface area and ease of uptake by the mucosal surface. U.S. Pat. No. 6,071,497, herein incorporated by reference, describes a pulmonary drug delivery system based on the formation of diketopiperazine microparticles as well as polymer-based microparticles.

SUMMARY OF THE INVENTION

Methods are provided for forming a coating of active agent on crystalline microparticles. In general, microparticles are coated with an active agent by modifying the surface properties of the microparticles such that the active agent has a higher affinity for the microparticle surface than for remaining in solution.

The present invention to provide improved methods for coating crystalline particles such as fumaryl diketopiperazine (FDKP) microparticles with active agents, such as proteins, using electrostatically, hydrophobically, or hydrogen-bond driven associations. In the present invention, liquid can optionally be removed (for recovery of active agent coated microparticles) by filtration or drying, or replaced by exchanging for a different solution medium. In any case, removal of the liquid medium is not an obligatory step in formation of the active agent-microparticle complex. This invention discloses a method for microparticle coating based on changing the surface properties of the crystalline microparticles to achieve adsorption of active agent to the microparticle.

In particular embodiments of the present invention, there is provided a method of coating a preformed crystalline microparticle in suspension with an active agent comprising; i) adjusting the energetic interaction between the active agent and the crystalline microparticle independent of solvent removal; and ii) allowing time for the active agent to adsorb onto the surface of the microparticle. In some embodiments, the method of coating a preformed crystalline microparticle in suspension with an active agent can further comprise a step of removing or exchanging the solvent without substantial effect on the interaction between active agent and microparticle.

In other particular embodiments of the present invention, the method of coating the microparticle with active agent is accomplished by modifying the surface properties of the microparticle. Modification of the surface properties of the microparticle is achieved by altering solution conditions. These conditions, in a non-limiting manner, comprise changing the pH. In other embodiments of the invention, the surface properties of the microparticle are modified by: 1) altering the polarity of the solution; 2) the addition of monovalent or multivalent ions; and 3) chemical derivatization of the microparticle.

In yet another embodiment, the present invention further comprises a step of dissolving the active agent in the fluid phase of the suspension of microparticles and subsequently changing the pH. Such step of dissolving the active agent in a fluid phase refers to the dissolving of a solid. In addition, such step of dissolving the active agent refers to the addition of a more concentrated solution of the active agent in addition to adding solid.

In still yet another embodiment, the pH conditions of the microparticle suspension are altered to favor interactions between active agent and microparticle prior to, or after, the addition of active agent.

In other embodiments, the active agent has more than one type of energetically favorable interaction with the microparticle surface.

In another particular embodiment of the present invention, the active agent is insulin or an analog thereof.

In other particular embodiments of the present invention, the surface properties that create a favorable interaction between the active agent and microparticle are selected from the group consisting of electrostatic properties, hydrophobic properties, and hydrogen bonding properties.

In another embodiment of the present invention, the microparticle is porous and has interior surfaces accessible to the bulk fluid of the solution. In one embodiment, the microparticle comprises a diketopiperazine such as fumaryl diketopiperazine but is not limited to such.

In embodiments of the present invention, the method of coating produces a monolayer of active agent on the microparticle surface. In other embodiments of the invention, the monolayer is continuous. In other embodiments of the invention, the active agent in the monolayer can have a preferred orientation.

In yet another embodiment, a method is provided for coating a pre-formed crystalline microparticle in suspension with insulin comprising adjusting the energetic interaction between the active agent and the crystalline microparticle independent of solvent removal; and absorbing the insulin onto the surface of the microparticles.

Solvent, as used herein, refers to the fluid medium in which the active agent and microparticle are "bathed." It should not be interpreted to require that all components are in solution. Indeed in many instances it may be used to refer to the liquid medium in which the microparticles are suspended.

BRIEF DESCRIPTION OF THE DRAWINGS

The following drawings form part of the present specification and are included to further demonstrate certain aspects of the examples disclosed herein. The invention may be better understood by reference to one or more of these drawings in combination with the detailed description of specific embodiments presented herein.

FIG. 4 depicts the pH dependence for the adsorption of active agents onto FDKP microparticles according to the teachings of the present invention.

FIG. 7 depicts the saturation curves for adsorption of the active agent onto FDKP microparticles according to the teachings of the present invention. Loading curves are shown for active agent/FDKP microparticles as a function of active agent concentration at pH 5.0.

FIG. 8 depicts adsorption of active agents onto microparticles at pH 5.0 as influenced by increasing concentrations of salt according to the teachings of the present invention. The active agent was added to the microparticle suspension after pH adjustment, unbound agent was filtered away and the microparticles dissolved to release bound agent.

DETAILED DESCRIPTION OF THE INVENTION

Agents to be Delivered

The substance to be coated onto the crystalline microparticle is referred to herein as the active agent. Examples of classes of active agent include pharmaceutical compositions, synthetic compounds, and organic macromolecules that have therapeutic, prophylactic, and/or diagnostic utility.

Generally, any form of active agent can be coated onto the surface of a crystalline microparticle. These materials can be organic macromolecules including nucleic acids, synthetic organic compounds, polypeptides, peptides, proteins, polysaccharides and other sugars, and lipids. Peptides, proteins, and polypeptides are all chains of amino acids linked by peptide bonds. Peptides are generally considered to be less than 30 amino acid residues, but may include more. Proteins are polymers that can contain more than 30 amino acid residues. The term polypeptide as is know in the art and as used herein, can refer to a peptide, a protein, or any other chain of amino acids of any length containing multiple peptide bonds, though generally containing at least 10 amino acids. The active agents used in the coating formulation can fall under a variety of biological activity classes, such as vasoactive agents, neuroactive agents, hormones, anticoagulants, immunomodulating agents, cytotoxic agents, antibiotics, antiviral agents, antigens, and antibodies. More particularly, active agents may include, in a non-limiting manner, insulin and analogs thereof, growth hormone, parathyroid hormone (PTH), ghrelin, granulocyte macrophage colony stimulating factor (GM-CSF), glucagon-like peptide 1 (GLP-1), Texas Red, alkynes, cyclosporins, clopiogrel and PPACK (D-phenylalanyl-L-prolyl-L-arginine chloromethyl ketone), antibodies and fragments thereof, including, but not limited to, humanized or chimeric antibodies; F(ab), F(ab)$_2$, or single-chain antibody alone or fused to other polypeptides; therapeutic or diagnostic monoclonal antibodies to cancer antigens, cytokines, infectious agents, inflammatory mediators, hormones, and cell surface antigens. Non-limiting examples of antibodies to tumor antigens include anti-SSX-$2_{41-49}$ (synovial sarcoma, X breakpoint 2), anti-NY-ESO-1 (esophageal tumor associated antigen), anti-PRAME (preferentially expressed antigen of melanoma), anti-PSMA (prostate-specific membrane antigen), anti-Melan-A (melanoma tumor associated antigen), anti-tyrosinase (melanoma tumor associated antigen), and anti-MOPC-21 (myeloma plasma-cell protein).

Delivery System—Crystalline Microparticles

Essentially, the term "microparticle" refers to a particle with a diameter of about 0.5-1000 μm, irrespective of the precise exterior or interior structure. Within the broad category of microparticles, "microspheres" refers to microparticles with uniform spherical shape. Crystalline microparticles as used herein refers to microparticles that have the internal structure though not necessarily the external form of a crystal and have a regular arrangement of atoms in a space lattice. Ionizable crystalline surfaces refer to crystalline microparticles that have the additional capacity to carry an electrical charge.

Preferably, the chemical substance composing the crystalline microparticle is reversibly reactive with the active agent to be delivered, as well as non-toxic and not metabolized, at least by rodents and humans. In addition, the crystalline structure of preferred microparticles is not substantially disrupted in the process of coating with active agent. The composition of the crystalline microparticle determines what type of chemical interactions can be manipulated to drive adsorption of an active agent to the microparticle surface.

A number of substances can be used to form crystalline microparticles. Microparticles as such have an outer surface, the properties of which can be manipulated in the coating process. Representative materials from which crystalline microparticles can be formed include but are not limited to: aromatic amino acids, salts with limited solubility in a defined pH range such as diketopiperazines and morpholine sulfates.

U.S. Pat. Nos. 5,352,461 and 5,503,852, herein incorporated by reference in their entirety, describe a drug delivery system based on formation of diketopiperazine (DKP) microparticles from diketopiperazine derivatives such as 3,6-bis[N-fumaryl-N-(n-butyl)amino] (also referred to as fumaryl diketopiperazine or FDKP; also termed (E)-3,6-bis[4-(N-carboxy-2-propenyl)amidobutyl]-2,5-diketopiperazine) that are stable at low pH and dissolve at the pH of blood or the small intestine. As disclosed in the above patents, the drug to be delivered is combined or loaded with the diketopiperazine particles by forming DKP microparticles in the presence of drug (payload). A system based on diketopiperazine structural elements, or one of its substitution derivatives, including, but not limited to, diketomorpholines and diketodioxanes, forms microparticles with desirable size distributions and pH ranges as well as good payload tolerance. A wide range of stable, reproducible characteristics can be generated with appropriate manipulations of the substituent groups.

Other diketopiperazines that may be contemplated in the present invention may include 3,6-di(4-aminobutyl)-2,5-diketopiperazine; 3,6-di(succinyl-4-aminobutyl)-2,5-diketopiperazine (succinyl diketopiperazine or SDKP); 3,6-di(maleyl-4-aminobutyl)-2,5-diketopiperazine; 3,6-di(citraconyl-4-aminobutyl)-2-5-diketopiperazine; 3,6-di(glutaryl-4-aminobutyl)-2,5-diketopiperazine; 3,6-di(malonyl-4-aminobutyl)-2,5-diketopiperazine; 3,6-di(oxalyl-4-aminobutyl)-2,5-diketopiperazine and derivatives therefrom. Diketopiperazine salts may also be utilized in the present invention and may included, for example, a pharmaceutically acceptable salt such as the Na, K, Li, Mg, Ca, ammonium, or mono-, di- or tri-alkylammonium (as derived from triethylamine, butylamine, diethanolamine, triethanolamine, or pyridines, and the like). The salt may be a mono-, di-, or mixed salt. Higher order salts are also contemplated for diketopiperazines in which the R groups contain more than one acid group. In other aspects of the invention, a basic form of the agent may be mixed with the diketopiperazine in order to form a drug salt of the diketopiperazine, such that the drug is the counter cation of the diketopiperazine.

U.S. Pat. Nos. 6,444,226, and 6,652,885, each herein incorporated by reference in their entirety, describes preparing and providing microparticles of DKP in aqueous suspension to which a solution of active agent is added, and then the critical step of lyophilizing the suspension to yield microparticles having a coating of active agent. The basis for this formulation is that the coating of microparticle with active agent is driven by removal of the liquid medium by lyophilization. (See also U.S. Pat. No. 6,440,463 which is incorporated herein by reference in its entirety). In contrast to teachings in the prior art, the present invention provides means for adjusting the association of active agent with the microparticle prior to solvent removal. Thus, removal of the liquid medium by bulk physical methods (e.g., filtration or sedimentation) or evaporative methods (e.g., lyophilization or spray-drying) can result in comparable loads.

Controlled Coating of Crystalline Microparticles

Controlled coating refers to the directed process of adsorbing active agent onto the surface of a crystalline microparticle. The coating process involves changing the surface properties of crystalline microparticles in a fluid suspension either by changing solution conditions (such as pH, temperature, polarity, ionic strength, and co-solvents), by complexation to mono- or multi-valent ions, or by chemical derivatization. Altering the surface properties of the microparticle either before or after addition of active agent affects its chemical interactions with active agent, thereby resulting in adsorption of active agent to the crystalline microparticle. Chemical interaction between the microparticle and active agent drives adsorption and results in a monolayer of the active agent on the surface of the microparticle. Once a molecule of active agent is adsorbed, that portion of the microparticle surface is not exposed for further interaction and adsorption of additional active agent at that particular surface point. The resulting monolayer can be either continuous (no gaps between adsorbed active agent molecules over the accessible surface) or non-continuous (gaps of exposed microparticle surface between adsorbed active agent molecules.

Adsorption of Active Agent onto Microparticles

As discussed above, adsorption of the active agent onto the microparticle results in mono-layering (coating) of the active agent onto the microparticle. However, there is more than one mechanism at play in the adsorption of an active agent, such as insulin for example, to crystalline microparticles:

The monolayer of an active agent, such as insulin, that coats the microparticle is one stage of the loading process of insulin onto the microparticle but is not necessarily the end result in the loading process as both monomeric and multimeric layers can be formed based on the energetics of the system.

Under conditions of permissive solubility, such as low insulin concentration and/or low pH (substantially below pH 5.0), attractive forces between insulin and the FDKP particle surface are much greater than the self-associative forces for insulin. Thus coating of insulin onto the microparticle occurs in a monolayer manner and saturation is observed without aggregation or multilayering onto the microparticle surface (see Example 6). As solubility approaches saturation, due to high insulin concentration and/or pH close to 5.0 (a solubility minimum for wild-type insulin), insulin self-association becomes more energetically favorable. Thus coating can proceed past the point of a saturated monolayer and further layers of insulin can be added to the particle. Two forms of self-association can be recognized: multimerization and aggregation. Multimerization is characterized by specific intermolecular interactions and fixed stoichiometry. Aggregation is characterized by unspecific intermolecular interactions and undefined stoichiometry. Speaking generally, multimeric active agents can be adsorbed in the multimeric state, or disassociated into monomers, or lower order multimers, and adsorbed to the surface in that state. In either case aggregation can mediate layering of the active agent onto the microparticle. According to the inventors current understanding, under the general conditions used in the examples of the present disclosure (such as dissolution of insulin in acetic acid) deposition of additional layers of insulin proceed as aggregation of non-hexameric insulin.

Method for Coating Microparticles

The procedure for coating crystalline microparticles, such as preformed crystalline microparticles, with active agents is described generally as follows: crystalline microparticles previously formed by precipitation, or another method, are suspended in liquid medium, such as water; and the medium is adjusted to alter the particles' surface either before or after addition of active agent. At this point the active agent will adsorb to the microparticle surface and after an interval of time (for example <1, 1, 2, 3, 4, 5, 6, 7, 8, 9, or 10 minutes; preferably from <1 to at least 5 minutes) the loading process will be complete. The liquid medium may be removed by any means including filtration, centrifugation, lyophilization or spray-drying or replaced by media exchange. Adsorption may be confirmed by either of two experimental approaches: 1) demonstrating the absence of significant amounts of active agent in a filtrate or supernatant and/or 2) demonstrating presence of the active agent in the solid phase while showing that active agent does not precipitate when taken through the same procedure in the absence of the microparticles.

Manipulating Microparticle Surface Properties

As disclosed elsewhere herein, the surface properties of the microparticle can be manipulated by various means. The microparticle surface properties that can be manipulated include, but are not limited to, electrostatic, hydrophobic, and hydrogen bonding properties. In various embodiments these manipulations are carried out in the absence or presence of the active agent, or before or after the microparticles and the active agent are mixed together. When the manipulation takes place in the presence of the active agent, for example by altering solution condition, there can also be effects on the active agent that will modify its affinity for the surface. Thus in some embodiments of the present invention, coating of the microparticle can involve manipulation of surface properties and modification of properties of the active agent. Methods directed to the latter are disclosed in co-pending U.S. patent application Ser. No. 11/532,065 entitled METHOD OF DRUG FORMULATION BASED ON INCREASING THE AFFINITY OF ACTIVE AGENTS FOR CRYSTALLINE MICROPARTICLE SURFACES filed on date even with the instant application and which is incorporated herein by reference in its entirety.

Electrostatic interactions are attractions between opposite charges or repulsions between like charges that grow stronger as the charges come closer to each other. Electrostatic interactions constitute a key component in understanding interactions between charged bodies in ionic solutions. For example, the stability of colloidal particles dispersed in a solvent can be explained by considering the competition between repulsive electrostatic interactions and the attractive van der Waals interactions. Also, the chemical functionality (for example, but not limited to COOH, NH, etc.) of the microparticle surface can be utilized as the counter ion to an ionized active agent such that the active agent/particle composite comprises a salt. Electrostatic interactions are also of importance when considering interaction and adhesion between particles.

Altering the pH of the surrounding solution system can change electrostatic properties of ionizable crystalline microparticles in suspension. As demonstrated in Example 3, changing the pH of the solution changes the ionization of a microparticle such that active agent adsorbs to the microparticle surface. Specifically, Example 4 shows that microparticles composed of FDKP (3,6-bis[N-fumaryl-N-(n-butyl)amino]2,5-diketopiperazine) are ionizable. The microparticles are insoluble in water below pH 3.5 but solubility increases rapidly between pH 3.5 and 5.0, presumably due to the ionization of the carboxyl groups. The FDKP microparticle is partially ionized at pH 5 prior to complete dissolution at higher pH, which can be observed indirectly via ultrasonic spectroscopy. Example 5 demonstrates the controlled coating of protein onto the FDKP microparticle surface. In one embodiment, diketopiperazine microparticles are suspended in an acidic solution, active agent is added to the suspension, and the pH of the solution is raised after the active agent and microparticles are mixed together. The increased pH alters the surface properties of the microparticles to create an environment in which the active agent has a higher affinity for the microparticle than for the solvent.

Alternatively, the pH of the microparticle suspension can be raised immediately prior to addition of active agent to the solution. The surface charge properties of the microparticle are altered by the change in pH such that active agent has a higher affinity for the microparticle than for remaining in solution and is adsorbed to the microparticle surface upon addition.

Examples 6 and 7 demonstrate loading of insulin onto FDKP particles by manipulation of pH conditions. Finally, the saturation of the microparticle by protein adsorption and the formation of a monolayer are described in Example 6.

Other Methods of Manipulating the Surfaces of Microparticles

In addition to electrostatic properties, other properties of a microparticle surface can be exploited to control adsorption of active agent. Microparticles containing compounds with imidazole, pyridine, Schiff bases, ketone, carboxylic acid bioisosteres, amides, or other functional groups that can exist in multiple structures could be manipulated to modify surface properties.

Hydrophobic interactions are associations of non-polar groups with each other in aqueous solutions because of their insolubility in water. Hydrophobic interactions can affect a number of molecular processes including, but not limited to, structure stabilization (be it of single molecules, complexes of two or three molecules, or larger assemblies) and dynamics, and make important contributions to protein-protein and protein-ligand binding processes. These interactions are also known to play a role in early events of protein folding, and are involved in complex assembly and self-assembly phenomena (e.g., formation of membranes).

Hydrophobic interactions can be manipulated by changing the protonation of crystalline microparticles composed of histidine. Protonating the histidine will reduce the nucelophilicity of the crystalline microparticles and impart a positive charge.

Hydrogen bonding interactions are especially strong dipole-dipole forces between molecules; a hydrogen atom in a polar bond (e.g., H—F, H—O or H—N) can experience an attractive force with a neighboring electronegative molecule or ion, which has an unshared pair of electrons (usually an F, O or N atom on another molecule). Hydrogen bonds are responsible for the unique properties of water and are very important in the organization of biological molecules, especially in influencing the structure of proteins and DNA.

In the present invention, the hydrogen bonding properties of the microparticle surface can be controlled by chemical derivatization. Hydrogen bond donors/acceptors can be added chemically to alter the microparticle surface. For example, the hydrogen in an N—H bond can undergo hydrogen bonding to the oxygen in a C═O bond. If the N—H is replaced by an N—CH$_3$, then this particular hydrogen bonding interaction is removed. Likewise, replacement of the C═O group with a C═C group also removes this particular bonding interaction.

Microparticles with surfaces containing ionizable aromatic groups are polar when ionized but hydrophobic in their un-ionized state. Starting with protonated surfaces and manipulating solution conditions to reduce particle surface ionization causes hydrophobic or aromatic active agents to coat the microparticle surface.

Microparticles with ketone surface groups could be manipulated by changing the solution polarity. By reducing solvent polarity (adding low polarity organic solvents to an aqueous solution) the enol-form is made the predominant species at the particle surface. This enol-form is a hydrogen bond donor whereas the keto-form is a hydrogen bond acceptor. The adsorption of nitrogen-containing drugs onto the microparticle surface is promoted in this manner.

Microparticles with surface groups that undergo pH- or temperature-induced isomerization can also be induced to adsorb drug molecules by manipulating solution conditions. In the case of these surfaces, the introduction of a kink in a linear surface group due to isomerization increases the mobility (fluidity) of the groups at the microparticle surface. This allows the surface to form more contacts with the active agent than are possible with an ordered surface. If the additional interactions with the active agent are each favorable, then the net interaction energy becomes favorable and the drug adsorbs to the microparticle surface.

Fluid Medium Removal Techniques

Removal of solvent after controlled coating of the crystalline surfaces with active agent can be achieved by methods including, but not limited to, sedimentation, filtration, or drying. Drying techniques include, but are not limited to, lyophilization and spray-drying. These techniques are known to those skilled in the art. In one embodiment of the present invention, solvent is removed by spray-drying. Methods of spray-drying diketopiperazine microparticles are disclosed in, for example, U.S. Provisional Patent Application No. 60/776,605 filed on Feb. 22, 2006, incorporated by reference herein for all it contains regarding spray-drying diketopiperazine microparticles.

Analysis of Surface Property Modifications

The present invention employs the technique of ultrasonic spectroscopy to analyze the changes in the surface properties of crystalline microparticles in a fluid suspension, which promote or enhance adsorption of an active agent to the crystalline microparticle. As disclosed elsewhere herein, such changes involve changing solution conditions (such as pH, temperature, polarity, ionic strength, and co-solvents), by complexation to mono- or multi-valent ions, or by chemical derivatization to alter the surface properties of the microparticle either before or after addition of active agent.

Ultrasonic spectroscopy is an analytical tool known to the skilled artisan. In brevity, ultrasonic spectroscopy employs sound waves. In particular, it uses a high frequency acoustical wave which probes intermolecular forces in samples/materials. Oscillating compression (and decompression) in the ultrasonic wave causes oscillation of molecular arrangements in the sample, which responds by intermolecular attraction or repulsion.

Traveling through samples, the ultrasonic wave loses its energy (a decrease in amplitude) and changes its velocity. This decrease in amplitude and change in velocity are analyzed as characteristics of the sample. Therefore, propagation of ultrasonic waves is determined by ultrasonic velocity and attenuation.

Ultrasonic velocity is determined by the elasticity and the density of the medium. Solids have the strongest interactions between the molecules followed by liquids and gases and are therefore more rigid compared with liquids and gases. Ultrasonic attenuation is a measure of the energy that ultrasonic waves lose as they traveling through a sample. It characterizes the ultrasonic transparency of the sample and can be seen as a reduction of amplitude of the wave.

Multi-frequency measurement of ultrasonic attenuation in homogeneous systems allows the analysis of fast chemical reactions such as, but not limited to, proton exchange, structural transitions (e.g., isomerization), self-association (e.g., dimerization), aggregation, binding of ligands to macromolecules etc.

EXAMPLES

The following examples are included to demonstrate embodiments of the present invention. It should be appreciated by those of skill in the art that the techniques disclosed in the examples which follow represent techniques discovered by the inventor to function well in the practice of the present invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

General Procedure for Loading Microparticles with Active Agents

Table 1 below is an example of electrostatically driven coating of an ionizable crystalline microparticle (FDKP microparticles) utilizing pH-controlled adsorption. In these experiments, FDKP microparticle suspensions were prepared at pH 2.0 and 4.5. Protein (growth hormone) was then added to each to give final conditions of 5 mg/mL FDKP particles and 200 μg/mL protein. After mixing, the bulk liquid was removed from suspension by filtration. The material trapped on the filter was then dissolved and collected. The protein concentration in all of the fractions was quantitated by HPLC.

At low pH (2.0), the protein did not adsorb to the particles and all protein was found in the first filtrate. By increasing the pH to 4.5, the surface properties of the particles were changed to have a high affinity for the protein. Under these conditions, the protein bound to the microparticles and was not seen in the filtrate. To determine the amount of protein associated with the microparticles, the protein was recovered when the microparticles were dissolved. The particle-free controls demonstrate that the protein, by itself, was not retained on the filter under the conditions used, i.e., the protein did not self-associate or otherwise aggregate into particles larger than the filter pores.

TABLE 1

Protein concentrations in an adsorption experiment with FDKP microparticles.

| Fraction | pH 2.0 with particles | pH 2.0 no particles | pH 4.5 with particles | pH 4.5 no particles |
|---|---|---|---|---|
| Initial conc. (μg/mL) | 200 | 200 | 200 | 200 |
| Filtrate (unbound protein) | 146 | 181 | 0 | 145 |
| Dissolved Particles | 0 | 0 | 180 | 0 |

Values shown are results from HPLC quantitation of the solutions after filtration

Example 2

Controlling FDKP Microparticle Ionization by Manipulating the pH

FDKP is a rod-shaped molecule with a carboxylic acid functional group at each end which is essentially insoluble in water below pH 3.5 when the carboxylic acids are protonated and carry no charge. The solubility of FDKP increases rapidly above pH 3.5 corresponding to ionization of the carboxyl groups. Modeling of FDKP crystals, which form as plates with two large, flat faces and narrow edges, indicates that the rod-like FDKP molecules align perpendicular to the edges of the plates so that the carboxylic acid ends of the molecule are arrayed on the large faces of the plates. On a theoretical basis, the surfaces of FDKP crystals should be partially ionized around pH 5.0, where the solubility is about 1 mg/mL, just below the pH at which a 10 mg/mL suspension of microparticles will dissolve.

Figure 1:
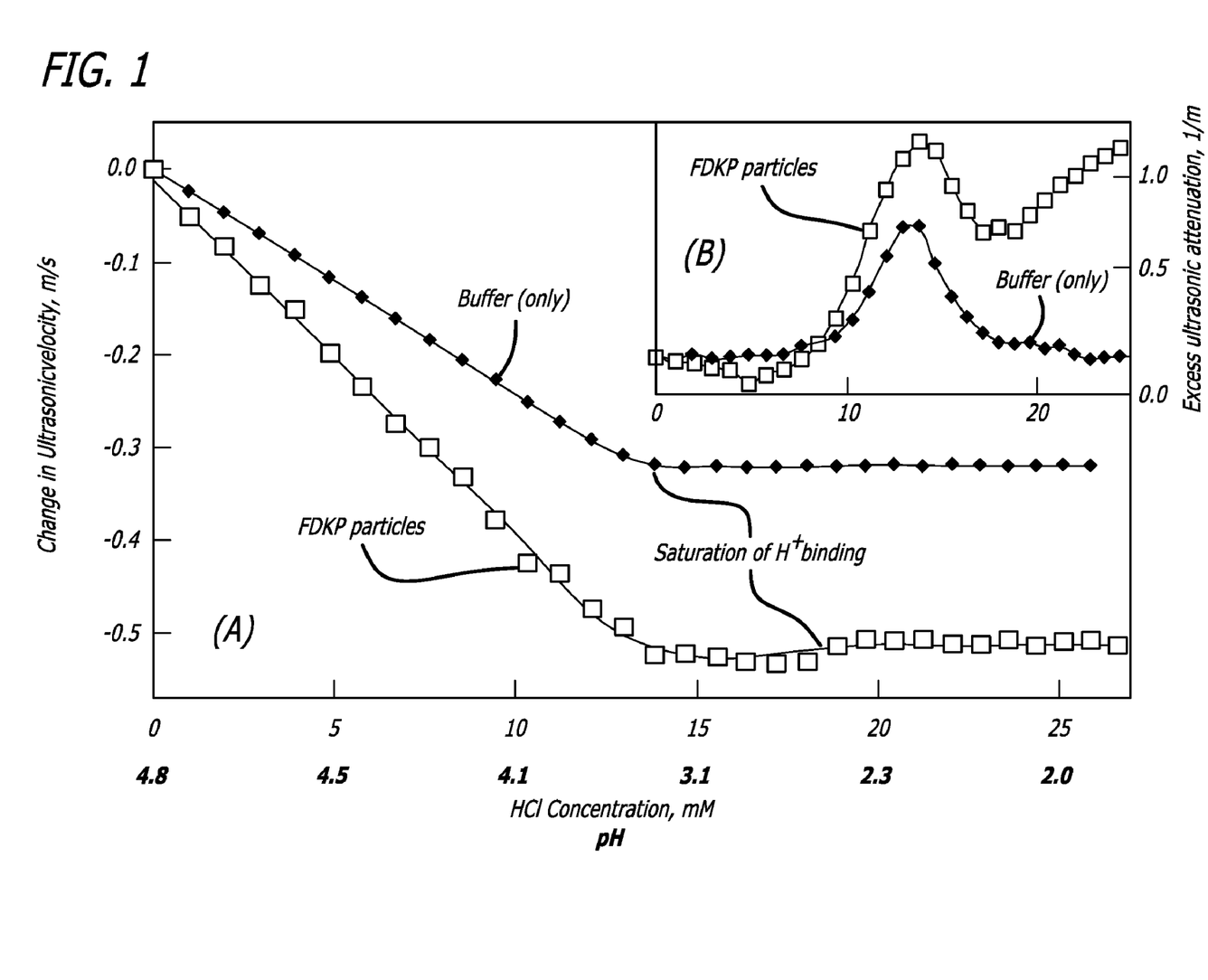
FIG. 1 depicts the ultrasonic HCl titration profiles for separate components of fumaryl diketopiperazine (FDKP) suspension, FDKP particles and buffer, according to the teachings of the present invention. The magnitude of the changes in ultrasonic velocity titration profile (FIG. 1; Panel A) reflects hydration changes caused by protonation of ionizable carboxylate groups of the sample components. The excess ultrasonic attenuation peaks (FIG. 1; Panel B) result from fast relaxation in the proton exchange reaction at the point of saturation. Frequency (F) is 15 MHz, temperature is 25° C.
Figure 2:
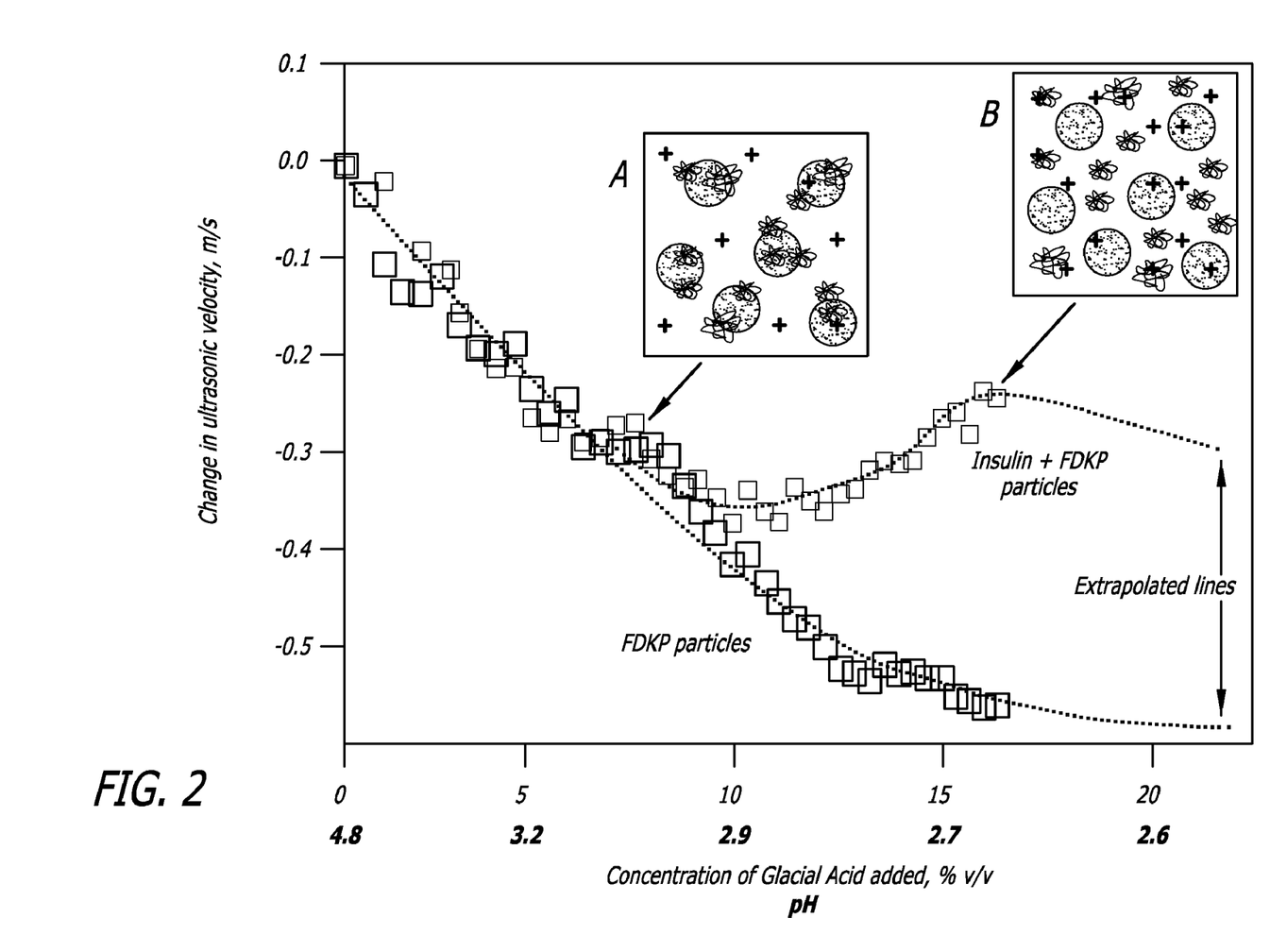
FIG. 2 depicts the ultrasonic glacial acetic acid titration profiles for FDKP particles+insulin and FDKP particles alone according to the teachings of the present invention. The ultrasonic velocity profile was calculated by subtracting the insulin contribution; frequency is 8 MHz, temperature is 25° C. Excess ultrasonic attenuation as a function of the concentration of glacial acetic acid added is also depicted. Two stages of glacial acetic acid induced acidification are similar to that observed by HCl titration. The inset panel on the left (Panel A) depicts the association of the active agent with the FDKP microparticle at pH greater than about 2.9. The inset panel on the right (Panel B) depicts the reduced interaction between the active agent and the microparticle at pH below about 2.9.
Figure 3:
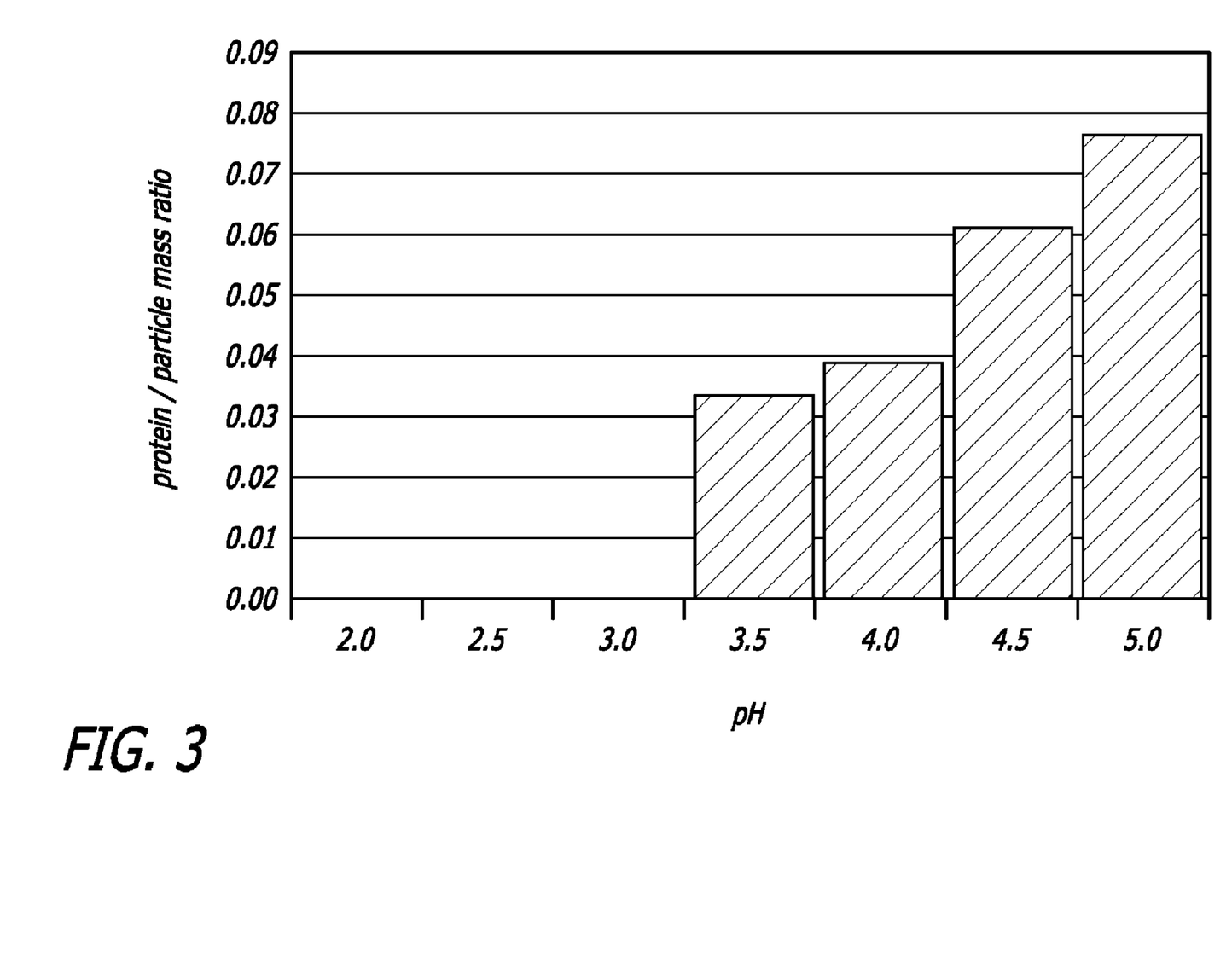
FIG. 3 depicts protein adsorption onto ionizable microparticles according to the teachings of the present invention. Protein was added to the microparticle suspension after pH adjustment, unbound protein was filtered away and the microparticles dissolved to release bound protein.

The ionization of FDKP crystal surfaces has been observed indirectly with ultrasonic spectroscopy. In FIG. 1, the ultrasonic titration curve of FDKP microparticles and buffer are shown. In this experiment, a solution containing 200 mM HCl was added in small aliquots to a stirred 10 mg/mL suspension of FDKP microparticles in 20 mM ammonium acetate buffer. The initial pH was 4.8. After each addition of HCl, the system was permitted to equilibrate and ultrasonic data was collected.

The decrease in ultrasonic velocity observed with increasing acid concentration (decreasing pH) reflects the protonation of carboxylic acid groups in the system. As the groups were protonated and became uncharged, the water structure around them relaxed and ultrasonic waves were transmitted more slowly (the ultrasonic velocity decreases). Because FDKP microparticles carboxylate surfaces and the carboxylate group in the acetate buffer are chemically very similar, the curves were also similar. The differences, however, were caused by the FDKP microparticles. First, the magnitude of the velocity change with FDKP microparticles was larger. This difference results from protonation of ionized carboxylate groups on the FDKP microparticle surface. The peak in the attenuation curve, which occurs near the point of complete protonation, was shifted to slightly higher acid concentration in the FDKP suspension. Finally, both FDKP parameters continued to change as the pH was reduced from 3.5 to 2.3. These changes reflect additional modifications in the surface properties of the particles that may include ordering of the surface carboxyl groups or other microstructural modifications.

Example 3

Loading Protein onto FDKP Microparticles by pH Manipulation of the Surface Properties The adsorption of proteins onto ionizable microparticle surfaces by pH manipulation can be achieved in two ways. The protein can be added and then the pH adjusted to cause ionization of the surface with concomitant adsorption of protein. This process is reversible. Alternatively the pH of the particle suspension can be adjusted to cause ionization of the surface before the protein is added.

The ultrasonic titration data shown in FIG. 2 indicates the association of protein (insulin) with the FDKP microparticles at pH greater than about 2.9 and reduced interaction at pH below about 2.9.

A suspension of FDKP microparticles was prepared in 20 mM ammonium acetate buffer, pH 4.8, and combined with an insulin stock solution to give 800 μL of suspension with a final concentration of 10 mg/mL FDKP microparticles and insulin concentration of 1 mg/mL. This suspension was introduced into an ultrasonic spectrometer. While stirring gently, glacial acetic acid was gradually added in 5 μL aliquots to lower the pH. At each step in the titration ultrasonic data was collected.

The change in ultrasonic velocity was related (proportional) to the amount of surface area (hydration water) of the particles and/or macromolecules in the sample. FIG. 2 illustrates that above pH of about 2.9 (10% v/v acetic acid added), the velocity curves for microparticles alone (FDKP particles) and microparticles with insulin (FDKP particles+Insulin) coincided. This indicated that the amount of surface area in the system is essentially the same as the surface area of FDKP microparticles alone. The insulin had a negligible contribution because it is very small compared to the microparticles. Below pH 2.9, the FDKP particles and FDKP particles+Insulin curves diverged. Ultrasonic velocity of the FDKP particles+Insulin curve was higher here, which indicated that there was more surface area exposed to water than in the FDKP particles alone sample. This additional surface area was from free insulin in the suspension. As the pH increased from about 2.7 to about 2.9, the insulin surface area was lost by adsorption of insulin to FDKP microparticle surfaces, and the higher intensity of the FDKP microparticles+Insulin curve disappeared as free insulin disappeared from the system.

As noted above, the second pH-driven method of coating particles with protein is to suspend particles in a fluid medium and adjust solution conditions to ionize the particle surface. The protein can then be added to the suspension and protein molecules will immediately adsorb. FIG. 3 illustrates the amount of protein (insulin) that was adsorbed upon addition to pH-adjusted suspensions of FDKP microparticles.

FDKP microparticle suspensions were prepared at 5 mg/mL and an excess of protein (2 mg/mL) was added. (An excess of protein, as referred to herein, is that amount over what is believed to be necessary to form a monolayer covering the accessible surface of the FDKP microparticle). After incubation, non-adsorbed protein was removed by filtration. The solids retained on the filter (retentate) were dissolved and the amounts of FDKP microparticles and protein retained on the filter were quantitated by HPLC. The protein/particle mass ratio was determined from this quantitation. Based on the known surface area of these particles and the molecular dimensions of the protein, a continuous monolayer of adsorbed protein was estimated to occur at a mass ratio of about 0.07. On the basis of that estimate it can be seen from this example that a continuous monolayer was formed at pH 5.0 and that non-continuous monolayers formed at pH 3.5 through pH 4.5.

Additionally, different lots of dried active agent-coated FDKP microparticles were suspended in either an acid solution (final pH about 2.0) or water (final pH about 4.5). The different active agents included insulin, growth hormone and insulin aspart (a fast-acting type of insulin), as shown in Table 2. The solvent was filtered from these suspensions and the retained particles were dissolved and collected. The amount of active agent in all of these samples was quantitated by HPLC. The results are shown in Table 2.

For each of the lots, the active agent was released from the particles in the acidic solution. Therefore, by protonating the surfaces of the microcrystals, the active agent desorbs from the crystal surfaces. When the particles were resuspended in water, which does not change the ionization state of the particle surface, the protein remained adsorbed.

TABLE 2

Active agents coated onto FDKP microparticles

|  | Growth Hormone | Insulin | Insulin Aspart |
|---|---|---|---|
| Active Agent Standard solution | 250 | 1103 | 1099 |
| Resuspended in Acidic solution | 240 | 980 | 893 |
| Redissolved after filtering away acidic solution | 0 | 49 | 29 |
| Resuspended in water | 0 | 4 | 0 |
| Redissolved after filtering away water | 191 | 936 | 982 |

Values in the table are integrated peak areas from HPLC quantitation (mAU * sec at 215 nm).

Example 4

Characterization of pH Driven Adsorption of Insulin onto FDKP Microparticles

Figure 4A:
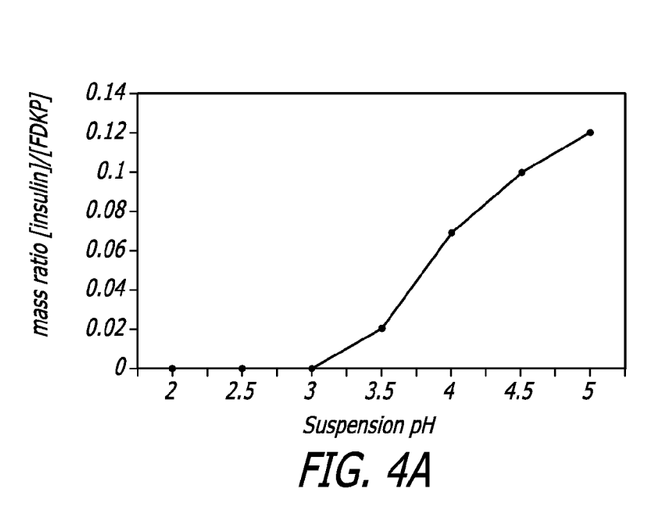
FIG. 4A depicts insulin adsorption.
Figure 4B:
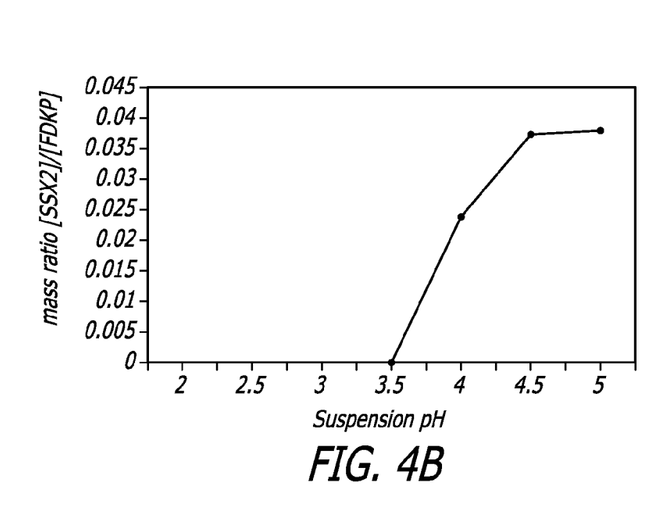
FIG. 4B depicts anti-SSX-$2_{41-49}$ monoclonal antibody adsorption.
Figure 4C:
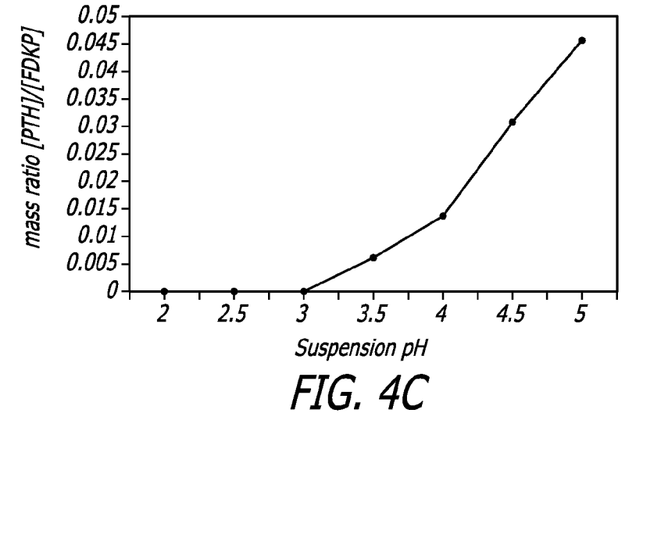
FIG. 4C depicts parathyroid hormone (PTH) adsorption and FIG. 4D depicts ghrelin adsorption.
Figure 4D:
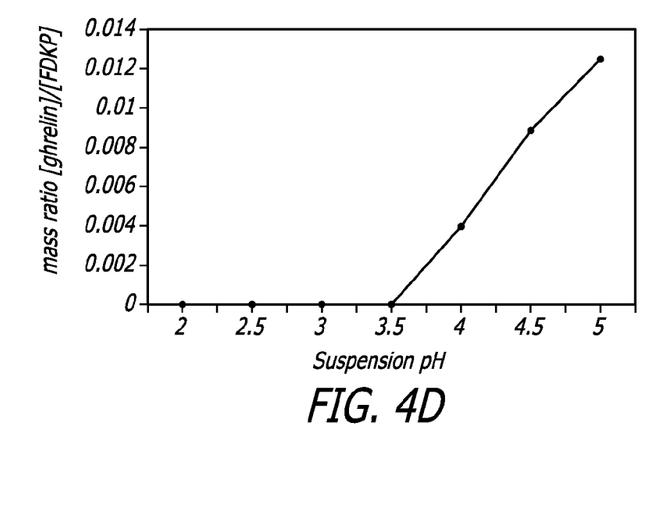

Insulin was adsorbed (loaded) onto FDKP microparticles in a pH-controlled process by mixing an aqueous suspension of FDKP microparticles with an aqueous solution of insulin. To characterize the effect of pH on insulin binding to FDKP microparticles, a 5 mg/mL suspension of FDKP particles at varying pH values was prepared. An excess of dissolved insulin was then added, allowed to adsorb for about 5 minutes, after which the unbound insulin was removed by filtration. The solid particles with adsorbed insulin were recovered from the filter (retentate), dissolved and collected. The amounts of insulin and dissolved FDKP microparticles were quantitated by HPLC. The amount of adsorbed insulin was calculated as a fraction of the total mass of retentate. The pH dependence of insulin adsorption is shown in FIG. 4A; insulin adsorption increased as a function of pH. Similar results were obtained for SSX-2$_{41-49}$ monoclonal antibody, PTH, and ghrelin as illustrated in FIGS. 4B, C, and D respectively.

Figure 5:
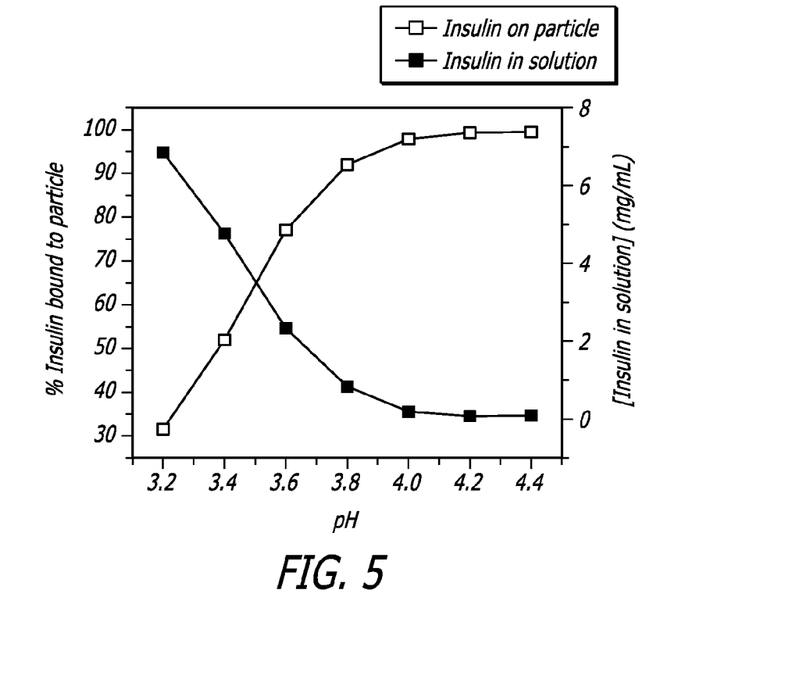
FIG. 5 depicts the pH dependence of insulin adsorption onto FDKP microparticles with limiting insulin concentration according to the teachings of the present invention.

Additionally, FDKP particles were suspended in insulin solutions (10 mg/mL) of different pHs. The mass ratio of FDKP particles to insulin was 10:1. The unbound insulin concentration in the supernatant was determined by HPLC after the supernatant had been separated from the particles by centrifugation. Insulin binding was determined as the difference from the initial insulin concentration. The data reported in FIG. 5 demonstrate that increasing pH resulted in reduced insulin in solution and increased insulin content on the FDKP particles.

Thus, insulin binding to FDKP particles increases with increasing pH from about pH 3.0 up to about pH 5. Preferably, the insulin solution is added at pH 3.6 and under these conditions approximately 75% of the insulin is adsorbed from solution onto the particles. Insulin binding increases to >95% as pH increases to ≧4.0. Substantially complete binding is achieved at about pH≧4.2, preferably about 4.4. At pH higher than 5.0, the FDKP microparticles begin to dissolve and no longer retain the structure of a crystalline microparticle.

Example 5

Description of Loading FDKP Microparticles with Insulin

In a production scale format (2-5 kg), microparticles of FDKP are formed by acid precipitation with acetic acid and washed. An insulin solution at pH 3.6 is added to the FDKP particle suspension. The insulin stock solution is 10 wt % insulin and 2.5 wt % acetic acid (pH of approximately 3.6). Ammonium hydroxide is used to adjust the pH of the mixture to 4.5. Table 3 indicates the amounts of the various components per kilogram of formulation used to prepare particles containing ~11.4% insulin by weight. Polysorbate 80 can be incorporated during particle formation and can improve the handling characteristics of the final particles. Time is allowed for insulin adsorption onto the FDKP particles and to ensure thorough mixing. The mixture is then added dropwise to liquid nitrogen to flash freeze the suspension. The fluid medium is removed by lyophilization to produce FDKP particle/insulin bulk drug product. Alternatively the mixture is spray-dried. Table 4 indicates the amounts of the various components in the bulk product after removal of the fluid medium.

TABLE 3

Composition of FDKP particles/Insulin Batch Formula

| Component | 11.4% FDKP/Insulin (Grams per kg of formulation) |
|---|---|
| Insulin, USP | 114 g |
| FDKP | 870 g |
| Polysorbate 80, USP* | 34.8 g |
| Strong Ammonia Solution, NF | 572 g |
| Acetic acid (glacial), NF | 3680 g |
| Purified Water, NF | 179000 g |
| Nitrogen, NF | as needed |

TABLE 4

Composition of FDKP particles/Insulin

| Component | 11.4% FDKP/Insulin, process (Quantity per gram formulation) |
|---|---|
| Insulin, USP | 3.0 IU (0.11 mg) |
| FDKP | 0.87 mg |
| Polysorbate 80, USP* | 0.007 mg |
| Strong Ammonia Solution, NF | Removed during process |
| Acetic acid (glacial), NF | Removed during process |
| Purified Water, NF | 0.012 mg |
| Nitrogen, NF | Removed during process |

In Tables 3 and 4 above, NF denotes - National Formulary
*Polysorbate 80 content is estimated by an HPLC/MS assay.
**The FDKP/Insulin formulation contains about 1.2% residual water after lyophilization. Trace quantities of acetic acid and ammonium hydroxide may also be present.

Example 6

Saturation of Microparticle Surfaces by Protein (Formation of a Continuous Monolayer)

Figure 6:
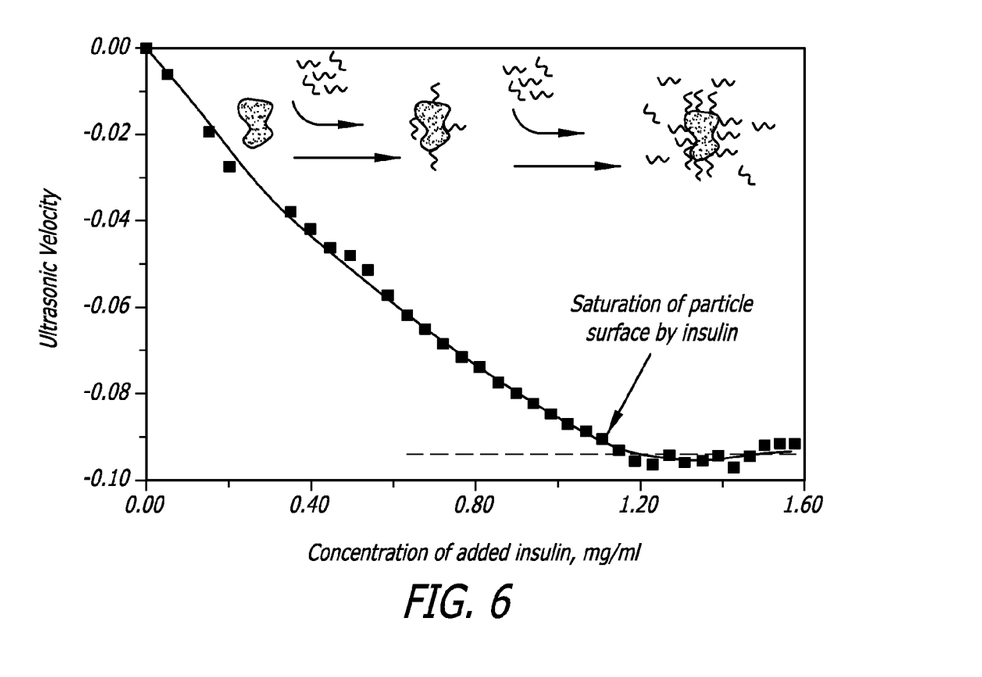
FIG. 6 depicts the change in ultrasonic velocity in FDKP microparticle suspension (11 mg/mL) upon stepwise titration of FDKP microparticles with protein (10 mg/mL) according to the teachings of the present invention. The contribution of free protein and the effect of FDKP microparticle dilution were subtracted. Temperature is 25° C.
Figure 7A:
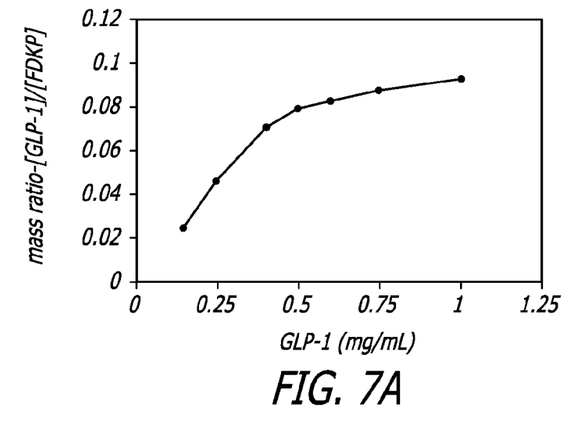
FIG. 7A depicts glucagon-like peptide 1 (GLP-1) adsorption.
Figure 7B:
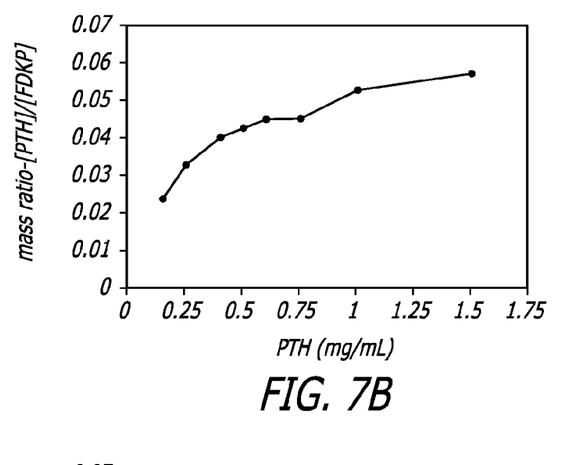
FIG. 7B depicts PTH adsorption.
Figure 7C:
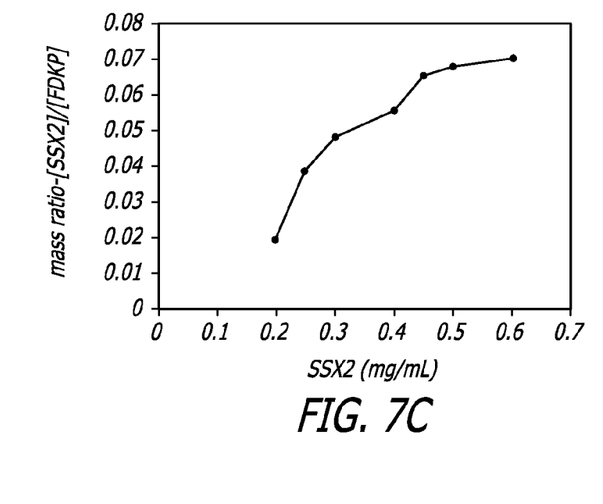
FIG. 7C depicts anti-SSX$2_{41-49}$ monoclonal antibody adsorption and FIG. 7D depicts anti-MOPC-21 monoclonal antibody adsorption.
Figure 7D:
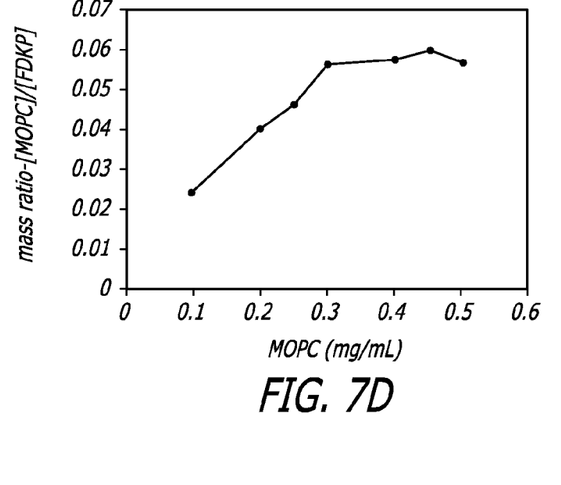
Figure 8A:
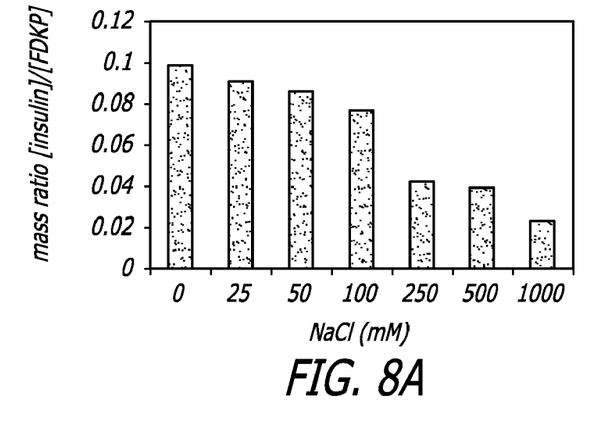
FIG. 8A depicts insulin adsorption.
Figure 8B:
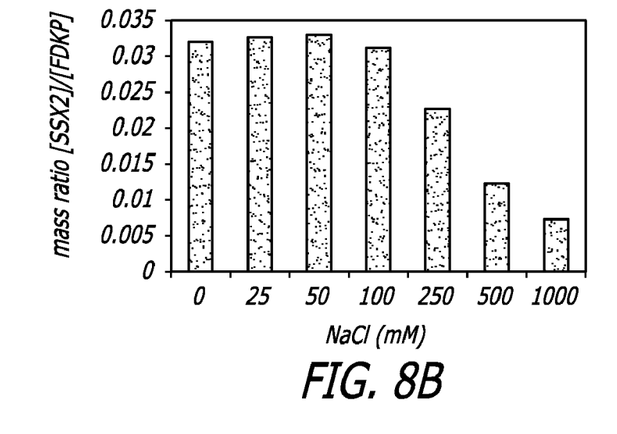
FIG. 8B depicts anti-SSX-$2_{41-49}$ monoclonal antibody adsorption.
Figure 8C:
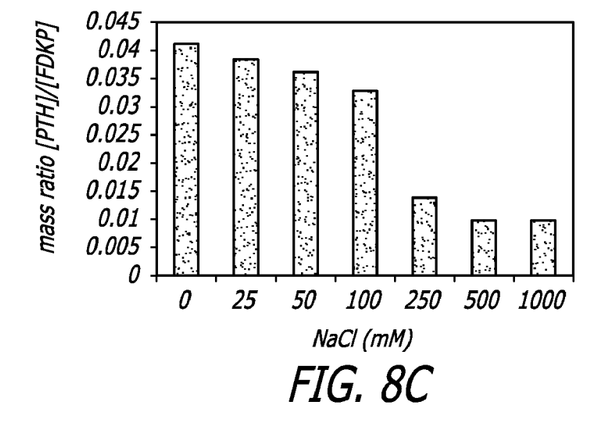
FIG. 8C depicts PTH adsorption and FIG. 8D depicts ghrelin adsorption.
Figure 8D:
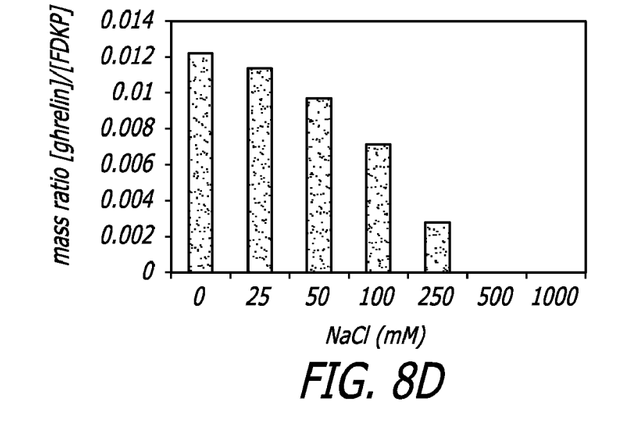

The surface coating of a microparticle with a monolayer should be a saturable process. That is, its accessible surface area and the diameter of the active agent molecule will dictate the capacity of the microparticle surface. FIG. 6 illustrates this saturation.

A suspension of FDKP microparticles was prepared and the pH was adjusted to between pH 3.0 and pH 3.5 at which point the surfaces partially ionize. In this procedure, higher pH could not be used because it would have caused self-association of the active agent, insulin. Small portions of a concentrated insulin solution were added to the stirred suspension. After each addition, the sample was allowed to stabilize and ultrasonic data was collected.

FIG. 6 shows that a reduction in ultrasonic velocity is observed as the protein concentration was increased. This type of change in the ultrasonic velocity is typical for ligand binding in aqueous solutions and indicates adsorption of the active protein to the FDKP microparticle surfaces. The velocity decrease results from the release of hydration water from the FDKP microparticle and protein surfaces. When the hydration water is displaced by adsorption of the active agent, its structure relaxes and produces a net decrease in the ultrasonic velocity through the sample. When all the binding sites on the surface of the FDKP microparticles have been saturated, i.e., a protein monolayer has formed, the curve levels off. Monolayer formation was also demonstrated by the data in FIGS. 7A-7D which showed that the adsorption of various active agents (GLP-1 [FIG. 7A]; PTH [FIG. 7B]; anti-SSX-$2_{41-49}$ monoclonal antibody [FIG. 7C]; and anti-MOPC-21 monoclonal antibody [FIG. 7D]), onto microparticles reached saturation as the concentration of the active agent is increased at a constant concentration of FDKP microparticles (5 mg/mL). These studies were conducted at pH 5.0 where optimal adsorption of the active agent to microparticles is observed. GLP-1 does not self associate at the concentrations used (as disclosed in U.S. Provisional Patent Application No. 60/744,882).

Example 7

Evidence for Electrostatic Interaction Mechanism

Evidence for an electrostatic mechanism of interaction is the ability to interfere with adsorption by weakening electrostatic interactions. This is demonstrated by adding salt to the ionized-particle/active agent system. FIGS. 8A-8D illustrate that increasing ionic strength in an active agent-FDKP microparticle system reduced the adsorption of the active agent onto the microparticle.

A series of samples were prepared at pH 5.0 where adsorption of the active agent onto FDKP microparticle surfaces is strong. Each sample contained a different quantity of salt (sodium chloride), as indicated under each bar in FIGS. 8A-8D (units are mM). The active agent was mixed into the suspension to give a final concentration of 5 mg/mL FDKP microparticles and 0.75 mg/mL insulin (an excess; FIG. 8A). After a brief incubation, unbound active agent was removed by filtration and the particles with adsorbed active agent were redissolved. The amount of active agent and particle recovered was quantitated by HPLC, and expressed as a mass ratio (% loading). FIGS. 8A-8D illustrate that increasing ionic strength in a active agent-FDKP microparticle system reduced the extent of adsorption of active agents including anti-SSX-$2_{41-49}$ monoclonal antibody (0.2 mg/mL; FIG. 8B), ghrelin (0.1 mg/mL; FIG. 8C) and PTH (0.25 mg/mL; FIG. 8D) in the presence of 5 mg/mL FDKP microparticles.

FIG. 8 shows an inverse correlation between the measured adsorption and the salt concentration in the loading suspension. This can be interpreted as evidence that the salt competed with the active agent for interaction with the particle surface. As the salt concentration was increased, it competed strongly and effectively for surface binding sites, and essentially displaced the active agent from the particle surfaces. It is also speculated, that decrease binding of the active agent to microparticle may be attributable to Debye shielding.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a" and "an" and "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed. No language in the specification should be construed as indicating any non-claimed element essential to the practice of the invention.

The use of the term "or" in the claims is used to mean "and/or" unless explicitly indicated to refer to alternatives only or the alternatives are mutually exclusive, although the disclosure supports a definition that refers to only alternatives and "and/or."

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is herein deemed to contain the group as modified thus fulfilling the written description of all Markush groups used in the appended claims.

Preferred embodiments of this invention are described herein, including the best mode known to the inventors for carrying out the invention. Of course, variations on those preferred embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above cited references and printed publications are herein individually incorporated by reference in their entirety.

Further, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

What is claimed:

1. A method for coating a preformed crystalline microparticle with an active agent in a suspension, said method comprising the steps in the sequence set forth of:
   i) obtaining a preformed crystalline diketopiperazine microparticle wherein said preformed crystalline diketopiperazine microparticle does not comprise an active agent;
   ii) providing a suspension comprising said preformed crystalline diketopiperazine microparticle, said active agent, and a solvent;
   iii) then altering suspension conditions in said provided suspension to modify an energetic interaction between said active agent and said preformed crystalline diketopiperazine microparticle wherein said altering suspension conditions is selected from the group consisting of altering the pH of the solvent, adding monovalent or multivalent ions, altering the polarity, and adding hydrogen bond donors or acceptors to modify a surface property of said preformed crystalline diketopiperazine microparticle wherein said altering step does not include a step of removing said solvent from said suspension; and
   iv) adsorbing said active agent onto a surface of said preformed crystalline diketopiperazine microparticle to provide a coating of said active agent on said crystalline microparticle without removing solvent from said suspension; wherein said altering step causes said adsorbing of said active agent onto a surface of said preformed crystalline diketopiperazine microparticle.

2. The method of claim 1 further comprising the step of removing or exchanging said solvent after said adsorbing step.

3. The method of claim 1 wherein said modified surface property comprises an electrostatic property.

4. The method of claim 1 wherein said modified surface property comprises a hydrophobic property.

5. The method of claim 1 wherein altering suspension conditions comprises altering the pH of said suspension.

6. The method of claim 1 wherein altering suspension conditions comprises adding monovalent or multivalent ions.

7. The method of claim 1 wherein altering suspension conditions comprises altering the polarity.

8. The method of claim 1 wherein altering suspension conditions comprises adding hydrogen bond donors or acceptors thereby modifying a surface property of said crystalline microparticle.

9. The method of claim 1 wherein said diketopiperazine crystalline microparticle comprises fumaryl diketopiperazine.

10. The method of claim 1 wherein said adsorbing produces a monolayer of said active agent on a surface of said crystalline microparticle.

11. The method of claim 1 wherein said adsorbing produces a continuous monolayer of said active agent on a surface of said crystalline microparticle.

12. The method of claim 1 wherein said active agent comprises insulin, an insulin analog, or combinations thereof.

13. The method of claim 1 wherein said crystalline microparticle comprises pores and comprises interior surfaces accessible to said solvent.

14. The method of claim 10 or 11 wherein said active agent in said monolayer has a preferred orientation.

15. A method for coating a preformed crystalline microparticle with insulin in a suspension, said method comprising the steps in the sequence set forth of:
   i) dissolving said insulin in a solvent, wherein said insulin comprises insulin, an insulin analog or combinations thereof;
   ii) obtaining a preformed crystalline diketopiperazine microparticle wherein said preformed crystalline diketopiperazine microparticle does not comprise an active agent;
   iii) forming a suspension comprising said preformed crystalline diketopiperazine microparticle, said insulin, and said solvent;
   iv) then altering suspension conditions in said provided suspension to modify the energetic interaction between said insulin and said crystalline microparticle wherein said altering step modifies a surface property of said crystalline microparticle;
   v) adsorbing said active agent onto a surface of said crystalline diketopiperazine microparticle to provide a coating of said active agent on said crystalline diketopiperazine microparticle without removing solvent from said suspension and wherein said altering step causes said adsorption of insulin onto a surface of said crystalline microparticle; and
   vi) removing or exchanging said solvent after said adsorbing step.

16. The method of claim 15 wherein altering suspension conditions comprises altering the pH of said suspension.

17. A method for coating a preformed crystalline microparticle with insulin in a suspension, said method comprising the steps in the sequence set forth of:
   i) dissolving said insulin in a solvent, wherein said insulin comprises insulin, an insulin analog or combinations thereof;
   ii) obtaining a preformed crystalline diketopiperazine microparticle in a suspension, wherein said preformed crystalline diketopiperazine microparticle does not comprise an active agent;
   iii) altering suspension conditions in said preformed crystalline diketopiperazine microparticle suspension wherein said altering step modifies a surface property of said crystalline microparticle;
   iv) then forming a suspension comprising said surface-modified preformed crystalline diketopiperazine microparticle, said insulin, and said solvent wherein said altering step has modified the energetic interaction between said insulin and said crystalline microparticle;
   v) then adsorbing said active agent onto a surface of said crystalline microparticle to provide a coating of said active agent on said crystalline microparticle without removing solvent from said suspension and wherein said altering step causes said adsorption of insulin onto a surface of said crystalline microparticle; and
   vi) removing or exchanging said solvent after said adsorbing step.

18. The method of claim 17 wherein said altering step comprises altering the pH of said suspension.

* * * * *